United States Patent [19]
Broadhead

[11] Patent Number: 6,130,208
[45] Date of Patent: Oct. 10, 2000

[54] FORMULATION CONTAINING A NUCLEOTIDE ANALOGUE

[75] Inventor: Joanne Broadhead, Loughborough, United Kingdom

[73] Assignee: AstraZeneca UK Limited, London, United Kingdom

[21] Appl. No.: 09/125,165

[22] PCT Filed: Jun. 29, 1998

[86] PCT No.: PCT/SE98/01287

§ 371 Date: Aug. 12, 1998

§ 102(e) Date: Aug. 12, 1998

[87] PCT Pub. No.: WO99/02542

PCT Pub. Date: Jan. 21, 1999

[30] Foreign Application Priority Data

Jul. 11, 1997 [SE] Sweden .................................. 9702680

[51] Int. Cl.⁷ .................................................... A61K 31/70
[52] U.S. Cl. ................................................................ 514/47
[58] Field of Search ................................................. 514/47

[56] References Cited

FOREIGN PATENT DOCUMENTS

| | | |
|---|---|---|
| 0 520 748 A1 | 12/1992 | European Pat. Off. . |
| 0 619 119 A1 | 10/1994 | European Pat. Off. . |
| 2 423 811 | 12/1974 | Germany . |
| WO 94/18216 | 8/1994 | WIPO . |

OTHER PUBLICATIONS

WPIDS accession No. 83–57281, Iatron Laboratories: "Adenosine tri phosphate stablisation—by adding mono saccharide or polysaccharide to ATP soln. And freeze–drying" & JP,A,58074696, 830506*.

Derwent Abstract No. 89–645596; Japanese Patent No. 1,288,915A (Daussan & Cie).

*Primary Examiner*—Raymond Henley, III
*Attorney, Agent, or Firm*—Nixon & Vanderhye

[57] ABSTRACT

A pharmaceutical composition comprising a nucleotide analogue and one or more glass forming additives which is suitable for freeze drying.

9 Claims, No Drawings

FORMULATION CONTAINING A NUCLEOTIDE ANALOGUE

This is a 371 of PCT/SE98/01287 filed Jun. 29, 1998.

FIELD OF THE INVENTION

The present invention provides a pharmaceutical composition suitable for freeze-drying and a process for the preparation of the composition.

BACKGROUND TO THE INVENTION

Freeze drying is a well known process used to prepare storage stable compositions of pharmaceutical compounds which otherwise suffer degradation when stored in the presence of water, for example, because of disproportionation and/or hydrolysis. Examples of such pharmaceutical compounds include nucleotides. The problem is that freeze drying does not remove all the water from a composition containing such a pharmaceutical compound. The water which remains after freeze drying may destabilise the composition during storage.

Accordingly there is a need for compositions of pharmaceutical compounds such as nucleotides which when freeze dried are stable to long term storage.

SUMMARY OPF THE INVENTION

According to the invention there is provided a pharmaceutical composition comprising a nucleotide analogue and one or more glass forming additives.

A nucleotide is a compound comprising a purine or pyrimidine base attached to a pentosugar wherein one or more of the hydroxy groups of the pentosugar are phosphorylated by a mono- or polyphosphate. A nucleotide analogue for use in the invention is in general a compound in which one or more of the three moieties of which a nucleotide is comprised is modified, for example, by attachment of one or more substituents and/or by replacement of one or more of the skeletal atoms.

The nucleotide used in the invention is preferably a compound disclosed in WO 94/18216 which is a compound of formula (I):

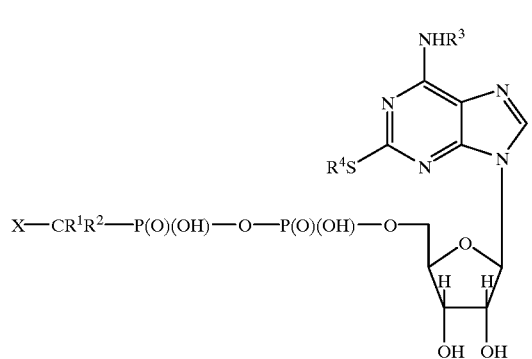

wherein $R^1$ and $R^2$ independently represent hydrogen or halogen, $R^3$ and $R^4$ independently represent phenyl, or $C_{1-6}$-alkyl optionally substituted by one or more substituents selected from $OR^5$, $C_{1-6}$-alkylthio, $NR^6R^7$, phenyl, $COOR^8$ and halogen, $R^5$, $R^6$, $R^7$ and $R^8$ independently represent hydrogen or $C_{1-6}$-alkyl, and X represents an acidic moiety, or a pharmaceutically acceptable salt thereof.

Compounds of formula (I) may exist in tautomeric, enantiomeric and diastereomeric forms, all of which are included within the scope of the invention.

Pharmaceutically acceptable salts of the compounds of formula (I) include alkali metal salts, e.g. sodium and potassium salts; alkaline earth metal salts, e.g. calcium and magnesium salts; salts of the Group III elements, e.g. aluminium salts; and ammonium salts. Salts with suitable organic bases, for example, salts with hydroxylamine; lower alkylamines, e.g. methylamine or ethylamine; with substituted lower alkylamines, e.g. hydroxysubstituted alkylamines; or with monocyclic nitrogen heterocyclic compounds, e.g. piperidine or morpholine; and salts with amino acids, e.g. with arginine, lysine etc, or an N-alkyl derivative thereof; or with an aminosugar, e.g. N-methyl-D-glucamine or glucosamine. The non-toxic physiologically acceptable salts are preferred, although other salts are also useful, e.g. in isolating or purifying the product.

Alkyl groups in the definitions of compounds of formula (I) include straight, branched or cyclic, saturated or unsaturated alkyl groups.

Halogens which $R^1$ and $R^2$ may represent include F, Cl, Br and I. Preferably $R^1$ and $R^2$ are the same and more preferably represent chloro.

Preferably $R^3$ and $R^4$ represent $C_{1-6}$-alkyl optionally substituted by one or more substituents selected from $OR^5$, $C_{1-6}$-alkylthio, $NR^6R^7$, phenyl, $COOR^8$ and halogen. Halogens with which $R^3$ and $R^4$ may be substituted include F, Cl, Br and I, and especially fluoro.

Particularly preferred are compounds in which $R^3$ represents $C_{1-6}$-alkyl optionally substituted by $C_{1-6}$-alkylthio. Particular alkyl groups that $R^3$ may represent include ethyl, propyl and butyl, and especially ethyl. Particular substituted alkyl groups that $R^3$ may represent include 2-(methylthio) ethyl.

Preferably $R^4$ represents $C_{1-6}$-alkyl optionally substituted by one or more, e.g. three, halogen atoms. Particular groups that $R^4$ may represent include propyl and 3,3,3-trifluoropropyl.

Acidic moieties which X may represent include Bronsted-Lowry acids, i.e. moieties which act as proton donors. The acidic moiety may be mono- or poly-acidic. Specific acidic moieties which may be mentioned include $—P(O)(OH)_2$, $—SO_3H$ and $—CO_2H$. Preferably X represents $—P(O)(OH)_2$.

In a particularly preferred embodiment of the invention, the nucleotide analogue is a compound of formula (Ia):

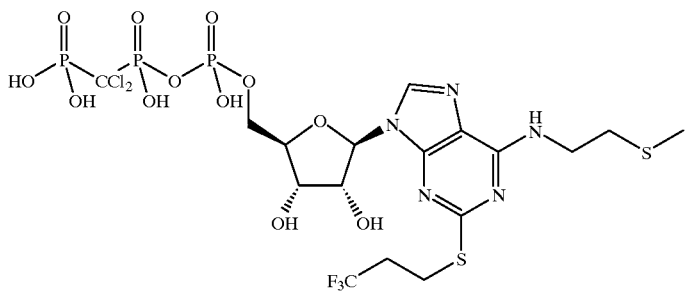

(Ia)

(which is N-[2-(methylthio)ethyl]-2-[(3,3,3-trifluoropropyl) thio]-5'-adenylic acid, monoanhydride with dichloromethylenebisphosphonic acid) or a pharmaceutically acceptable salt thereof, particularly the tetrasodium salt.

Compounds of formula (I) may be prepared using the methods disclosed in WO 94/18216.

The compounds of formula (I) are useful because they exhibit pharmacological activity in mammals and act as $P_{2T}$ receptor antagonists. Accordingly, the compositions of the invention are useful in therapy, especially adjunctive therapy, particularly they are indicated for use as: inhibitors of platelet activation, aggregation and degranulation, promoters of platelet disaggregation, anti-thrombotic agents or in the treatment or prophylaxis of unstable angina, coronary angioplasty (PTCA), myocardial infarction, perithrombolysis, primary arterial thrombotic complications of atherosclerosis such as thrombotic or embolic stroke, transient ischaemic attacks, peripheral vascular disease, myocardial infarction with or without thrombolysis, arterial complications due to interventions in atherosclerotic disease such as angioplasty, endarterectomy, stent placement, coronary and other vascular graft surgery, thrombotic complications of surgical or mechanical damage such as tissue salvage following accidental or surgical trauma, reconstructive surgery including skin and muscle flaps, conditions with a diffuse thrombotic/platelet consumption component such as disseminated intravascular coagulation, thrombotic thrombocytopaenic purpura, haemolytic uraemic syndrome, thrombotic complications of septicaemia, adult respiratory distress syndrome, anti-phospholipid syndrome, heparin-induced thrombocytopaenia and pre-eclampsia/eclampsia, or venous thrombosis such as deep vein thrombosis, venoocclusive disease, haematological conditions such as myeloproliferative disease, including thrombocythaemia, sickle cell disease; or in the prevention of mechanically-induced platelet activation in vivo, such as cardio-pulmonary bypass and extracorporeal membrane oxygenation (prevention of microthromboembolism), mechanically-induced platelet activation in vitro, such as use in the preservation of blood products, e.g. platelet concentrates, or shunt occlusion such as in renal dialysis and plasmapheresis, thrombosis secondary to vascular damage/inflammation such as vasculitis, arteritis, glomerulonephritis, inflammatory bowel disease and organ graft rejection, conditions such as migraine, Raynaud's phenomenon, conditions in which platelets can contribute to the underlying inflammatory disease process in the vascular wall such as atheromatous plaque formation/progression, stenosis/restenosis and in other inflammatory conditions such as asthma, in which platelets and platelet-derived factors are implicated in the immunological disease process.

According to the invention there is further provided the use of a composition according to the invention for the treatment of the above disorders. In particular the compositions of the invention are useful for treating acute coronary syndromes, myocardial infarction, thrombotic stroke, transient ischaemic attacks, peripheral vascular disease and angina, especially unstable angina. The invention also provides a method of treatment of the above disorders which comprises administering to a patient suffering from such a disorder a therapeutically effective amount of a composition according to the invention.

A glass forming modifying agent suitable for use in the present invention is generally one which has a glass transition temperature of above room temperature, more especially above about 50° C. in the dried state. This is in order that on storage under ambient conditions the dried composition is in glassy form. Examples of suitable modifying agents include sugars (for example sucrose, trehalose, lactose or sorbitol) or polymers (such as dextran or polyvinylpyrrolidone (PVP)). Particularly preferred examples of suitable modifying agents include sucrose. The amount of the modifying agent present in the composition according to the invention should be sufficient to stabilise the composition. The invention further provides a pharmaceutical composition in freeze dried, spray dried or vacuum dried form and in reconstituted form.

According to the invention there is further provided a process for the preparation of a composition according to the invention which comprises mixing the ingredients of the composition, and either freezing them and drying the frozen mixture, or spraying them (for example into warm air).

The advantage of the composition of the invention is that it is more stable to long term storage as demonstrated by the Example.

The water content of the dried formulation is preferably less than 5% by weight, more preferably less than 3% by weight.

The pharmaceutical composition according to the present invention optionally additionally comprises a pharmaceutically acceptable excipient, for example a chelating or sequestering agent, an antioxidant, a tonicity adjusting agent, a pH modifying agent and/or a buffering agent, for example one or more of those disclosed in "Review of Excipients and pH's for Parenteral Products used in the United States" Yu-Chang John Wang and R R Kowal, J Parenteral Drug Association, 34, 452–462 (1980).

The process for preparing the pharmaceutical composition according to the present invention may be carried out using any freeze-drying, vacuum drying or spray drying technique commonly used within the pharmaceutical area.

A preferred process according to the invention is a vial freeze-drying process. Such a process comprises filling sterile vials with a sterile filtered solution of the composition according to the invention. A sterile freeze-drying stopper is partially inserted into the vial which is frozen, e.g. at a temperature from −30 to −50° C., and thereafter vacuum dried in the frozen state. After drying the stopper is fully inserted before removing the vial from the lyophilization unit.

Upon use but before administration, the pharmaceutical compositions according to the present invention are generally reconstituted in a pharmaceutically acceptable diluent. Examples of pharmaceutically acceptable diluents for injection or infusion include water, saline (e.g. a 0.9% w/v sodium chloride solution for injection) and dextrose (e.g. a 5% w/v dextrose solution for infusion). Preferably water is used as the diluent.

The solution of the pharmaceutical composition according to the invention obtained after reconstitution can be an isotonic solution.

In a preferred embodiment the pH of the composition of the present invention is from 6 to 10, more preferably from 7 to 9.

The pharmaceutical composition according to the present invention when reconstituted is preferably administered by injection intravenously, subcutaneously or intramuscularly, preferably intravenously.

The compositions according to the invention may be packed in suitably adapted pharmaceutical application devices, for example syringes, vials or ampoules, such that the addition of water allows the in situ preparation of an aqueous solution of the active ingredient in a form suitable for immediate adminstration to the patient.

The invention will now be described in more detail by the following examples.

EXAMPLE 1

The freeze dried compositions listed in Table 1 were prepared as follows. For each batch the ingredients were dissolved in the specified volume of water and placed in a Virtis Genesis 25EL freeze drier. They were frozen to between −40° C. and −50° C. and then subjected to 60–80 hours primary drying at −35° C. to −40° C. The shelf temperature was then slowly increased to 35° C. and drying was completed by holding at his temperature for 12–14 hours. The vacuum was held at 100 mTorr throughout primary and secondary drying.

Compound Ia refers to N-[2-(methylthio)ethyl]-2-[(3,3,3-trifluoropropyl)thio]-5'-adenylic acid, monoanhydride with dichloromethylenebisphosphonic acid

TABLE 1

| Batch | Component | Amount % by wt/volume |
|---|---|---|
| 1 | Compound Ia | 3.7% w/v |
|   | Water | to 2 ml |
| 2 | Compound Ia | 1.85% w/v |
|   | Sucrose | 13.12% w/v |
|   | Water | to 3 ml |
| 3 | Compound Ia | 3.7% w/v |
|   | Sucrose | 11.28% w/v |
|   | Water | to 3 ml |
| 4 | Compound Ia | 3.33% w/v |
|   | Sucrose | 3.33% w/v |
|   | Water | to 3 ml |
| 5 | Compound Ia | 10% w/v |
|   | Sucrose | 10% w/v |
|   | Water | to 3 ml |

TABLE 1-continued

| Batch | Component | Amount % by wt/volume |
|---|---|---|
| 6 | Compound Ia | 3.33% w/v |
|   | Sorbitol | 11.17% w/v |
|   | Water | to 3 ml |
| 7 | Compound Ia | 3.33% w/v |
|   | Lactose | 11.17% w/v |
|   | Water | to 3 ml |
| 8 | Compound Ia | 3.33% w/v |
|   | Trehalose | 11.17% w/v |
|   | Water | to 3 ml |
| 9 | Compound Ia | 1.67% w/v |
|   | Trehalose | 13.03 w/v |
|   | Water | to 3 ml | wherein the analogue is a sodium salt of a compound of formula (Ia).

Each batch was then stored at 40° C. and 75% relative humidity and suffered the degradation shown in table 2.

TABLE 2

| Batch | Storage time | Impurity A | Impurity B | Total Impurities |
|---|---|---|---|---|
| 1 | 0 | 0.08 | 0.16 | 0.82 |
|   | 4 | 0.50 | 0.44 | 1.59 |
|   | 12 | 0.82 | 0.57 | 1.99 |
|   | 26 | 1.32 | 0.67 | 2.67 |
| 2 | 0 | 0.06 | 0.08 | 0.82 |
|   | 4 | 0.07 | 0.07 | 0.70 |
|   | 12 | 0.06 | 0.07 | 0.72 |
|   | 26 | 0.08 | 0.07 | 0.77 |
| 3 | 0 | 0.07 | 0.07 | 0.72 |
|   | 4 | 0.07 | 0.07 | 0.72 |
|   | 12 | 0.08 | 0.07 | 0.74 |
|   | 26 | 0.13 | 0.08 | 0.83 |
| 4 | 0 | 0.09 | 0.11 | 0.51 |
|   | 4 | 0.2 | 0.11 | 0.63 |
|   | 12 | 0.35 | 0.12 | 0.80 |
| 5 | 0 | 0.18 | 0.11 | 0.77 |
|   | 4 | 0.19 | 0.12 | 0.62 |
|   | 12 | 0.33 | 0.12 | 0.77 |
| 6 | 0 | 0.05 | 0.07 | 0.38 |
|   | 4 | 0.2 | 0.08 | 0.56 |
|   | 12 | 0.35 | 0.19 | 0.73 |
| 7 | 0 | 0.09 | 0.11 | 0.5 |
|   | 4 | 0.17 | 0.1 | 0.64 |
|   | 12 | 0.26 | 0.10 | 0.73 |
| 8 | 0 | 0.09 | 0.11 | 0.49 |
|   | 4 | 0.24 | 0.1 | 0.69 |
|   | 12 | 0.47 | 0.11 | 0.87 |
| 9 | 0 | 0.09 | 0.08 | 0.56 |
|   | 4 | 0.14 | 0.08 | 0.54 |
|   | 12 | 0.30 | 0.08 | 0.71 | wherein the amount of each impurity is a % by weight and impurity A is a compound of formula (Ib) which is

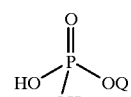

and impurity B is a compound of formula (Ic)

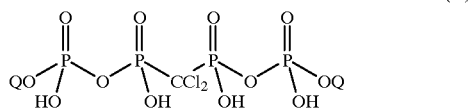

wherein Q represents

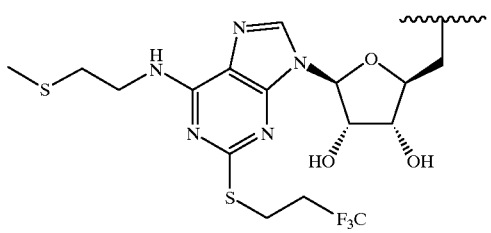

The data in Table 2 clearly shows that the compositions according to the invention are more stable to long term storage than compositions comprising only the analogue.

What is claimed is:

1. A pharmaceutical composition comprising a nucleotide analog and one or more glass forming additives, wherein the nucleotide is a compound of formula (I):

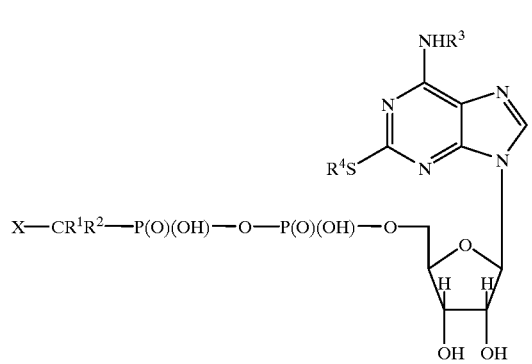

wherein $R^1$ and $R^2$ independently represent hydrogen or halogen, $R^3$ and $R^4$ independently represent phenyl, or $C_{1-6}$-alkyl optionally substituted by one or more substituents selected from $OR^5$, $C_{1-6}$-alkylthio, $NR^6R^7$, phenyl, $COOR^8$ and halogen, $R^5$, $R^6$, $R^7$ and $R^8$ independent represent hydrogen or $C_{1-6}$-alkyl and X represents an acidic moiety, or a pharmaceutically acceptable salt thereof.

2. A pharmaceutical composition according to claim 1 which is in freeze-dried, spray dried or vacuum dried form.

3. A pharmaceutical composition according to claim 1 which is in reconstituted form.

4. A pharmaceutical composition according to claim 1 and further including a modifying agent.

5. A pharmaceutical composition according to claim 4, in which the modifying agent is sucrose.

6. A method of treating a platelet aggregation disorder which method comprises treating a subject suffering from a said disorder with a therapeutically effective amount of a pharmaceutical composition as defined in claim 1.

7. A process for the preparation of a pharmaceutical composition according to claim 2 which process comprises mixing the ingredients of the composition, and either freezing them and drying the frozen mixture, or spray-drying them.

8. A method of treating acute coronary syndromes and percutaneous transluminal coronary angioplasty in a patient in need of said treatment, said method comprising the step of administering to said patient a therapeutically effective amount of a pharmaceutical composition as defined in claim 1.

9. A method of treating angina in a patient in need of said treatment, said method comprising the step of administering to said patient a therapeutically effective amount of a pharmaceutical composition as defined in claim 1.

* * * * *